US00PP11052P

United States Patent [19]

Zary

[11] Patent Number: Plant 11,052

[45] Date of Patent: Sep. 7, 1999

[54] HYBRID TEA ROSE PLANT NAMED 'JACREDI'

[75] Inventor: Keith W. Zary, Thousand Oaks, Calif.

[73] Assignee: Bear Creek Gardens, Inc., Medford, Oreg.

[21] Appl. No.: 09/001,456

[22] Filed: Dec. 30, 1997

[51] Int. Cl.[6] ..... A01H 5/00

[52] U.S. Cl. ..... Plt./139

[58] Field of Search ..... Plt./139, 140

[56] References Cited

U.S. PATENT DOCUMENTS

| | | | |
|---|---|---|---|
| P.P. 7,390 | 12/1990 | Meilland | Plt./139 |
| P.P. 8,290 | 7/1993 | Carmel | Plt./139 |
| P.P. 8,369 | 9/1993 | Suzuki | Plt./139 |

*Primary Examiner*—Howard J. Locker
*Attorney, Agent, or Firm*—Klarquist Sparkman Campbell Leigh & Whinston, LLP

[57] ABSTRACT

Hybrid tea rose plant having a vigorous, upright growth habit; very good production of bright red flowers on long straight stems; and which flowers have exceptionally long vase life.

1 Drawing Sheet

The present invention relates to a new and distinct variety of rose plant of the hybrid tea class which was originated by me by crossing the variety 'KORenlo,' (U.S. Plant Pat. No. 5,679), with an unnamed seedling.

The primary objective of this breeding was to produce a new rose variety having the high cut flower production and long vase life of the female parent combined with the bright red flower color and long stems of the unnamed red hybrid tea seedling. The objective was substantially achieved, along with other desirable improvements, as evidenced by the following unique combination of characteristics that are outstanding in the new variety and that distinguish it from its parents, as well as from all other varieties of which I am aware:

1. Very high cut flower production;
2. Exceptionally long cut rose vase life;
3. Bright red flowers;
4. Long, strong straight stems;
5. Vigorous, upright growth habit.

'JACredi' is a cut flower, greenhouse rose capable under Somis, Calif. conditions of producing 200–220 stems per square meter of greenhouse or 30 stems per plant. Stems range from 22–28" long. Vase life is exceptional at 18–21 days.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'KORenlo' (U.S. Plant Pat. No. 5,679).
*Pollen parent.*—Unnamed seedling.

Classification:

*Botanical.*—Rosa hybrida.
*Commercial.*—Hybrid tea.

Flower

Observations made from specimens grown in a greenhouse environment at Somis, Calif. from January 1996–August 1997.

Blooming habit: Continuous.

Bud:

*Size.*—One and three-quarters inches long when the petals start to unfurl.
*Form.*—The bud form is long, pointed ovoid.
*Color.*—When sepals first divide, bud color is Red Group 53A. When half blown, the upper sides of the petals are Red Group 45A; and the lower sides of the petals are closest to Red Group 53B.
*Sepals.*—Color: Green group 137D. Surface texture: Covered with fine hairs. There are three normally to heavily appendaged sepals. There are two unappendaged sepals with hairy edges.
*Receptacle.*—Color: Yellow-Green Group 146B. Shape: Funnel. Size: Small (5/16" long×3/16" wide). Surface: Smooth.
*Peduncle.*—Length: Medium (3½" to 4"). Surface: Smooth with a few glands. Color: Medium green. Strength: Stiff, erect.

Bloom:

*Size.*—Medium. Average open size is four inches.
*Borne.*—Singly.
*Stems.*—Long (22–28"), strong.
*Form.*—When first open: High centered. Permanence: Retains its form to the end; outer petal edges curl back with some quilling.
*Petalage.*—Number of petals under normal conditions: 35–40.
*Color.*—The upper sides of the petals are Red Group 45A. The reverse sides of the petals are Red Group 53B. The base of each petal has a small (3/16"×3/16") greenish-white half moon at the point of attachment. The major color on the upper side is Red Group 45A.
*Variegations.*—None.
*Discoloration.*—At the end of the first day: No change. At the end of the third day: No change. No change through ten days when petals begin to dry. In the vase no change for at least two weeks then a gradual change from Red Group 45A toward Red Group 53A, then 53B, then 53C. Total vase life is three weeks before the petals dry.

*Fragrance.*—None.

Petals:

*Texture.*—Thick.

*Shape.*—Round.

*Form.*—Tips slightly recurved, edges slightly quilled.

*Arrangement.*—Imbricated. Petaloids in the center are few.

*Persistence.*—Hang on and dry.

*Lastingness.*—On the plant: Very long (ten days before they dry). As a cut flower: Very long (three weeks before they dry).

Reproductive parts:

*Anthers.*—Size: Medium. Quantity: Many. Color: Yellow. Arrangement: Regular around styles.

*Filaments.*—Color: Reddish-brown.

*Pollen.*—Color: Lemon yellow.

*Styles.*—Color: Reddish.

*Stigmas.*—Color: Greenish-white.

Plant:

*Form.*—Bush.

*Growth.*—Very vigorous; upright; branching; Height six months after planting in a greenhouse in Somis, Calif. is six feet. By constant cutting of cut roses, height is kept at this level. Width is three feet.

*Foliage.*—Number of leaflets on normal mid-stem leaves: Five.

*Size.*—Medium (5 to 5½"×4 to 4½").

*Quantity.*—Abundant.

*Color.*—New foliage: Upper and lower surfaces: Greyed-Red Group 178B. Foliage quickly turns green. Old foliage: Upper surface: Green Group 139A. Lower surface: Green Group 138B.

*Shape.*—Pointed oval.

*Texture.*—Upper side: Leathery.

*Edge.*—Serrated.

*Serration.*—Single, small.

*Petiole rachis.*—Color: Green.

*Petiole underside.*—Smooth with occasional prickles.

*Stipules.*—Short (⅜"); serrated, bearded.

*Disease resistance.*—Resistant to mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—*Medium* (¼); hooked downward.

*Color when young.*—Red.

Small prickles:

*Quantity.*—*On main stalks: None. On laterals: None.*

I claim:

1. A new and distinct variety of rose plant of the hybrid tea class, substantially as herein shown and described, characterized particularly as to novelty by exceptionally long vase life; very good production of flowers per square meter of greenhouse; vigorous, upright growth habit; bright red flowers; and long, straight stems.

* * * * *

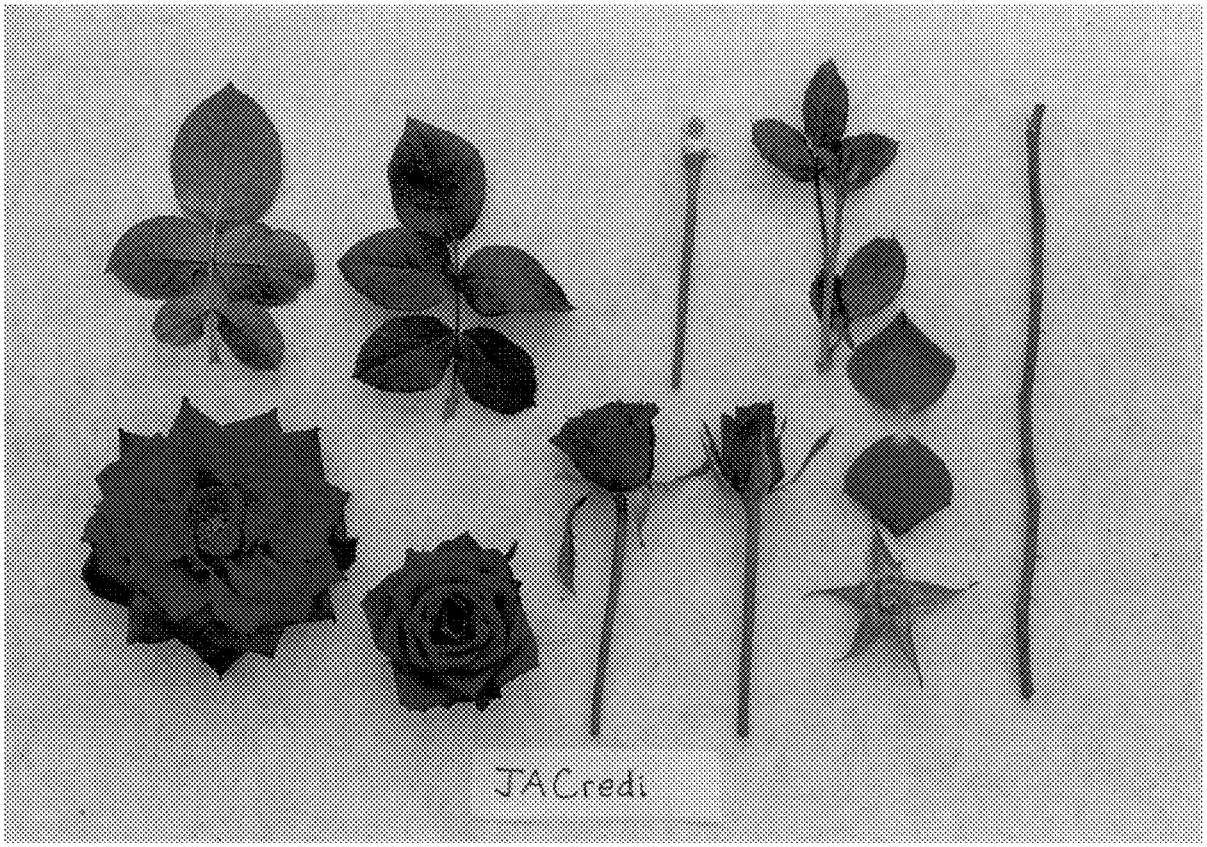
JACredi